United States Patent
O'Keefe et al.

(10) Patent No.: US 6,694,067 B1
(45) Date of Patent: Feb. 17, 2004

(54) CAVITY ENHANCED FIBER OPTIC AND WAVEGUIDE CHEMICAL SENSOR

(75) Inventors: Anthony O'Keefe, Cupertino, CA (US); James J. Scherer, San Mateo, CA (US)

(73) Assignee: Los Gatos Research, Mountain View, CA (US)

(*) Notice: Subject to any disclaimer, the term of this patent is extended or adjusted under 35 U.S.C. 154(b) by 324 days.

(21) Appl. No.: 09/755,925

(22) Filed: Jan. 5, 2001

(51) Int. Cl.$^7$ .............................. G02B 6/00; G02B 6/34
(52) U.S. Cl. ............................ 385/12; 385/37; 385/145
(58) Field of Search .............................. 385/12, 37, 15, 385/27, 31, 123, 129, 132, 141, 144, 145

(56) References Cited

U.S. PATENT DOCUMENTS

| | | | |
|---|---|---|---|
| 4,824,206 A | 4/1989 | Klainer et al. | 350/96.29 |
| 4,834,496 A | * 5/1989 | Blyler et al. | 385/12 |
| 4,846,548 A | 7/1989 | Klainer | 350/96.29 |
| 4,892,383 A | 1/1990 | Klainer et al. | 350/96.29 |
| 4,913,519 A | 4/1990 | Klainer et al. | 350/96.1 |
| 4,929,049 A | 5/1990 | Le Goullon et al. | 350/96.29 |
| 5,026,139 A | 6/1991 | Klainer et al. | 350/96.29 |

(List continued on next page.)

FOREIGN PATENT DOCUMENTS

| | | |
|---|---|---|
| WO | WO93/04368 | 3/1993 |
| WO | WO94/17388 | 8/1994 |
| WO | WO94/17556 | 8/1994 |
| WO | WO95/03539 | 2/1995 |
| WO | WO95/15496 | 6/1995 |
| WO | WO95/16052 | 6/1995 |
| WO | WO95/20051 | 7/1995 |
| WO | WO95/20151 | 7/1995 |

OTHER PUBLICATIONS

A. O'Keefe et al., "CW Integrated Cavity Output Spectroscopy", *Chemical Physics Letters*, vol. 307, Jul. 9, 1999, pp. 343–349.

A. O'Keefe et al., "Cavity Ring–Down Optical Spectrometer for Absorption Measurements Using Pulsed Laser Sources", *Rev. Sci. Instruments*, vol. 59(12), Dec. 1988, pp. 2544–2551.

A. O'Keefe, "Integrated Cavity Output Analysis of Ultra–Weak Absorption", *Chemical Physics Letters*, vol. 307, 1999, pp. 343–349.

C. Ronot, et al., "Detection of Chemical Vapours With a Specifically Coated Optical–Fibre Sensor", *Sensors and Actuators B* vol. II, 1993, pp. 375–381.

G. Stewart, et al., "Sensitivity Improvement for Evanescent–Wave Gas Sensors", *Sensors and Actuators B*, vol. II, 1993, pp. 521–524.

*Primary Examiner*—Rodney Bovernick
*Assistant Examiner*—Sarah U Song
(74) *Attorney, Agent, or Firm*—Thomas Schneck; Mark Protsik

(57) ABSTRACT

Chemically specific fiber and waveguide sensors are formed in a fiber optic or optical waveguide material in which injected light is trapped within a Bragg grating optical cavity. The Bragg cavity effectively traps the light for long times, corresponding to effective path lengths equal to hundreds or thousands of meters in the fiber or waveguide medium. The Bragg grating optical cavity is surrounded by a cladding of chemically sensitive material whose optical properties change when exposed to specific chemicals or classes of chemicals. The change in the optical properties of the cladding results in a change in the light trapping characteristics of the fiber or waveguide. Changes in optical transmission of the fiber optic or waveguide sensor can then be related to the concentration of specific chemicals or classes of chemicals in the environment surrounding the sensor.

9 Claims, 1 Drawing Sheet

U.S. PATENT DOCUMENTS

| | | | |
|---|---|---|---|
| 5,059,790 A | | 10/1991 | Klainer et al. .......... 250/227.21 |
| 5,065,401 A | * | 11/1991 | Scifres et al. ............ 372/29.02 |
| 5,066,133 A | | 11/1991 | Brienza ...................... 359/570 |
| 5,081,012 A | * | 1/1992 | Flanagan et al. ............ 435/7.9 |
| 5,082,629 A | * | 1/1992 | Burgess et al. .......... 422/82.11 |
| 5,094,958 A | | 3/1992 | Klainer et al. .............. 436/172 |
| 5,107,133 A | | 4/1992 | Klainer ....................... 250/573 |
| 5,109,442 A | | 4/1992 | Klainer et al. ................. 385/12 |
| 5,116,759 A | | 5/1992 | Klainer et al. .............. 435/288 |
| 5,165,005 A | | 11/1992 | Klainer et al. .............. 385/129 |
| 5,177,805 A | * | 1/1993 | Groger et al. ................. 385/12 |
| 5,253,037 A | | 10/1993 | Klainer et al. .............. 356/133 |
| 5,302,350 A | | 4/1994 | Goswami et al. ............. 422/86 |
| 5,324,933 A | | 6/1994 | Berkcan ................. 250/227.23 |
| 5,327,515 A | | 7/1994 | Anderson et al. ............ 385/123 |
| 5,346,671 A | | 9/1994 | Goswami et al. ............. 422/86 |
| 5,349,181 A | | 9/1994 | Saini et al. ............ 250/227.14 |
| 5,358,875 A | | 10/1994 | Goswami et al. ........... 436/124 |
| 5,405,583 A | | 4/1995 | Goswami et al. ............. 422/86 |
| 5,439,647 A | | 8/1995 | Saini ....................... 422/82.11 |
| 5,457,056 A | | 10/1995 | Dandge et al. ............. 436/166 |
| 5,528,040 A | | 6/1996 | Lehmann .................... 250/343 |
| 5,538,850 A | | 7/1996 | King et al. .................... 435/6 |
| 5,564,832 A | * | 10/1996 | Ball et al. .................... 374/161 |
| 5,591,407 A | * | 1/1997 | Groger et al. ........... 422/82.05 |
| 5,640,234 A | * | 6/1997 | Roth et al. .................. 356/128 |
| 5,650,123 A | | 7/1997 | Saini et al. .............. 422/82.11 |
| 5,698,848 A | * | 12/1997 | Belk ..................... 250/227.11 |
| 5,737,457 A | | 4/1998 | Saini et al. .................... 385/12 |
| 5,766,956 A | | 6/1998 | Groger et al. ............. 436/164 |
| 5,780,251 A | | 7/1998 | Klainer et al. ............. 435/7.93 |
| 5,891,658 A | | 4/1999 | Klainer et al. ............. 435/7.93 |
| 5,903,358 A | | 5/1999 | Zare et al. .................. 356/437 |
| 5,986,768 A | | 11/1999 | Pipino ........................ 356/440 |
| 6,035,082 A | | 3/2000 | Murphy et al. ............... 385/37 |
| 6,385,377 B1 | * | 5/2002 | Brueck et al. .............. 385/122 |

\* cited by examiner

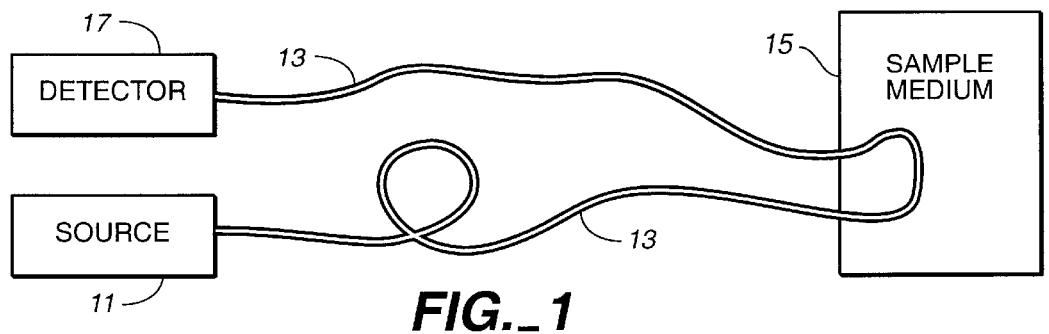
FIG._1
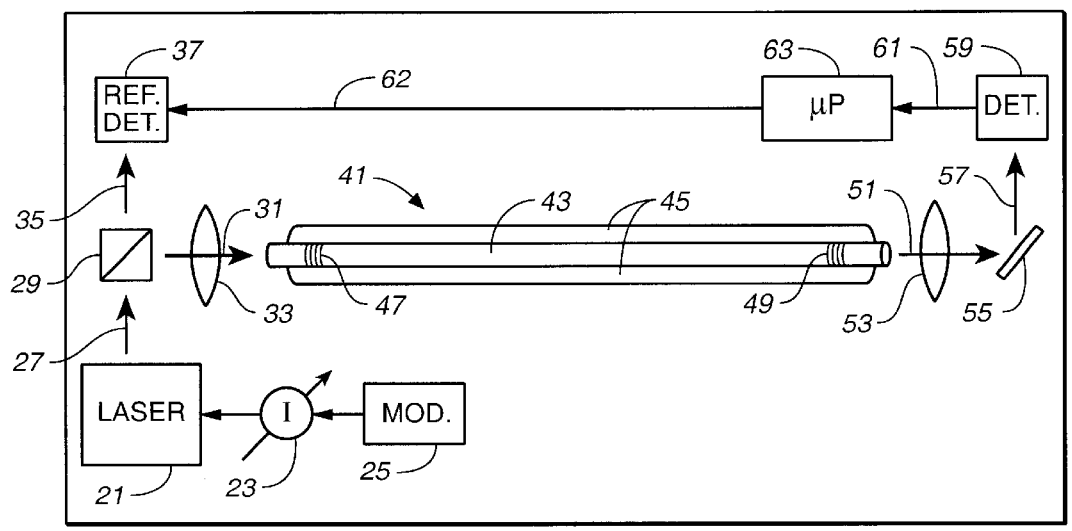
FIG._2
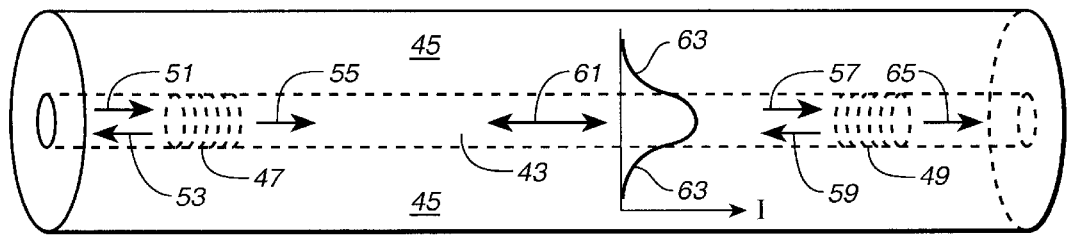
FIG._3

CAVITY ENHANCED FIBER OPTIC AND WAVEGUIDE CHEMICAL SENSOR

TECHNICAL FIELD

The present invention relates to chemical sensing to detect the presence or measure the amount or concentration of specific chemicals or classes of chemicals in the environment surrounding a sensor. The invention relates in particular to fiberoptic or optical waveguide chemical sensors, especially that class of chemical sensors which uses changes in optical transmission or absorption in the fiber or waveguide or evanescent wave emanating therefrom to sense the chemicals.

BACKGROUND ART

Detection and measuring of atomic and molecular trace chemical species using lasers dates to the 1980s. Because the various chemical species have unique absorption spectra, several forms of absorption spectroscopy have been developed to detect them at low levels (on the order of parts per billion) with short response times (on the order of microseconds) and with limited interference from the other chemical species that may be present. One such technique, ring-down cavity (RDC) spectroscopy, measures the absorption rate of a light pulse confined within a stable, low loss optical cavity. The cavity may be formed from a pair of highly reflective (R≧. 9999) mirrors in stable resonator configurations. Light from a pulsed laser tuned to match an absorption frequency of a chemical species of interest is coupled into the optical cavity through one mirror. If the pulse length is less than the cavity's round trip time, a small ($\sim 10^{-5}$) but stable fraction of the incident light enters the cavity and "rings" back and forth between the cavity mirrors. The number of photons trapped in the cavity slowly decays (rings down) due to the combined loss through the cavity mirrors and the presence of a chemical absorber and/or scattering in the cavity. For an empty cell, the decay time constant is $\tau = d/[c(1-R)]$, where d is the cavity length, c is the speed of light, and R is the average mirror reflectivity. When an atomic or molecular absorber is present in the cavity, the decay rate will be increased, with strong absorption resulting in a faster decay then weak absorption. At each round trip of the injected pulse, a small fraction ($\sim 10^{-5}$) of the intracavity light is transmitted through the back mirror and is detected by a sensitive photodetector such as a photomultiplier tube, with the time constant of the detector set long compared to the cavity round trip time, its output follows a smooth exponential decay that can be analyzed in the time domain to obtain the absorption coefficient of the chemical species in the cavity, and indirectly its concentration. An advantage of this ring down cavity technique is that it is highly sensitive, limited largely by the reflectivity of the cavity mirrors, and is insensitive to amplitude fluctuation between laser pulses. However, the laser wavelength must be matched to an absorption line of the chemical of interest. In practice, wavelength dependent ringdown signals are determined in a pointwise manner to determine the corresponding absorption spectrum for the species within the cavity. This data is then converted into species concentration using standard analytical methods.

The ring-down cavity spectroscopy technique can be modified to use a continuous-wave (cw) laser source in place of a pulsed laser source. Examples of such cw-laser-based spectroscopy instruments are described in U.S. Pat. No. 5,528,040 to Lehmann and U.S. Pat. No. 5,903,358 to Zare et al., as well as by Anthony O'Keefe et al. in Chemical Physics Letters 307, pp. 343–349 (Jul. 9, 1999). In one such cw laser technique, the laser frequency is scanned and ringdown decay events recorded to provide an absorption spectrum as a function of laser frequency. The radiation intensity in the cavity will build up when excited at a resonance frequency coinciding with a cavity mode and will ring down at a decay rate corresponding to the absorption by the sample gas when the optical frequency is modulated off of the cavity mode. In another cw laser technique, the optical frequency of the laser source is maintained at the resonance frequency of a cavity mode. The intracavity intensity builds up to a saturation value determined by the mirror reflectivity and sample gas absorption. An advantage of this technique is that there is higher intracavity power, but it requires that the cavity be stabilized. A third cw technique, described in the aforementioned paper of O'Keefe et al. in Chemical Physics Letters, uses dithering to avoid having to stabilize the cavity. The laser output is modulated rapidly over a frequency spacing containing several cavity modes, or one of the cavity mirrors is vibrated using a piezoelectric transducer to rapidly modulate the cavity modes, or both. The average transmission through the cavity is measured to obtain the effective absorption for the mirrors and chemical sample. The light trapped in the optical cavity passes through the absorbing sample many times, effectively amplifying the absorption signal. The resulting average change in the signal transmitted through the cavity is greatly enhanced over what would result from a single pass through the same sample pathlength. In a simple system, this enhancement is given by the inverse of the fractional mirror transmission. For a system comprised of two mirrors of identical reflectivity, R, this fractional transmission is T=1−R, and the absorption enhancement is 1/T. By addition to this simple system of a weak fractional absorption per cavity length, equal to k, the observed average absorption is equal to k divided by T. Because T is typically very small, in the range of 0.01 to 0.00001, the observed amplification of the absorption signal is large, ranging from 100 to 10000. This makes this very useful in measuring weak absorption signals. The observed transmission signal is recorded as a function of light source frequency, with and without sample to provide a complete quantitative spectrum.

All of these optical cavity techniques are very sensitive because they effectively multiply the sample path length by large factors. However, they are limited in their practical application to very clean gas samples only, because strong absorption or other attenuation mechanisms drive the system to saturation rapidly. Anything that scatters light, such as glass flow tubes or cells, turbulent samples (e.g. flames), or liquid samples, must be avoided, because any amount of scattering tends to interfere with accurate absorption measurement.

A different class of sensor is used to detect trace chemical species of interest in liquid and gas samples. In particular, sensors that employ fiber optics and optical waveguides are becoming increasingly common for applications where a chemical sensor needs to be introduced into a liquid medium, such as a storage tank or well. Fiber optics and optical waveguides make it possible to place a chemical sensor device in contact with the medium without needing to also insert the entire optical source and detector system. An optical fiber or waveguide 13 transmits light from a source 11 to the sample 15 and returns the optical signal to the detection system 17, as shown in FIG. 1. Such sensors employ a variety of means for producing a chemical detection signal.

Some devices employ a two-fiber or two-waveguide geometry made up of a source fiber or waveguide and a signal fiber or waveguide. For example, the source fiber may send a excitation optical signal to an end fiber piece containing an optical phosphor, producing a fluorescence signal that is sensitive to the presence of certain chemicals. The signal fiber is located relative to the source fiber and phosphor such that the resulting signal is partially collected and transmitted to a detector for measurement and analysis. One drawback of this scheme is that the quenching of the fluorescence signal is effected by many types of chemicals, so the number of chemical species that can be unambiguously sensed is limited.

Another fiber or waveguide-based approach uses evanescent wave effects to provide some overlap of the light propagating within the fiber or waveguide with the analyte sample in the surrounding liquid or gas environment or with an optical structure exposed to that environment such that propagation properties of the light are altered. In one device, described in U.S. Pat. No. 5,324,933 to Berkcan, the evanescent wave interacts, at a portion of the fiber where the cladding is thin, with a grating formed in a measured sensitive layer of a block exposed to the environment. Presence of the measured of interest in the environment causes the sensitive layer to swell, changing the Bragg condition of the grating and the wavelength of the fiber-guided light that is reflected by the grating. Optical detection of the reflected and transmitted light output from respective ends of the fiber measures wavelength shifts in that optical signal to determine the presence and concentration of the measurement.

Other evanescent wave schemes rely on direct absorption of the evanescent wave extending outside of the fiber or waveguide into the surrounding sample medium. Embodiments include bare fiber core variations and D-shaped fibers, as well as waveguide adaptations. (For example, see G. Stewart et al., Sensors and Actuators B, Vol. ii, pages 521–524, 1993.) The evanescent wave overlaps the surrounding medium and can be absorbed by a chemical specie of interest, the amount of absorption providing a measure of that chemical specie's concentration in the medium. One problem associated with these schemes is that the available fibers and waveguides limit the spectral bands that can be employed in practice to the near infrared region between 1 and 2 micrometers wavelength, but in this region most chemical of interest absorb light only in weak vibrational overtone bands. Because those absorptions are typically 50 to 100 times weaker than fundamental vibrational bands in the mid infrared region between 3 and 10 micrometers wavelength, sensitivity of fiber or waveguide-based direct absorption schemes is often much worse than non-fiber or waveguide absorption schemes. Moreover, the typical silicon glass fiber or waveguide core material has inherent absorptions that can obscure many weak absorptions arising from the evanescent effect, further degrading sensitivity.

An intrinsic optical fiber sensor which does not rely on direct optical absorption by a chemical is described in U.S. Pat. No. 4,846,548 to Klainer, and also by C. Ronot et al. in sensors and Actuators B, Vol. ii, pages 375–381, 1993. The optical cladding of an optical fiber is replaced by a thin chemically sensitive polymer which acts as the fiber's cladding. The cladding can be selected from any of a number of polymeric families, each with different responses to different chemicals. In particular, some polymers can rapidly absorb or react with different classes of organic chemicals from the near environment. If the polymer cladding absorbs a chemical present in the environment, the cladding's refractive index will change, leading to a change in the transmission of light through the optical fiber. (The change in transmission efficiency of the fiber is due to a change in the total internal reflection property of the core-cladding optical interface because of the refractive index change of the cladding.) Light from an LED or laser diode may be coupled into the fiber, and the amount of transmission monitored by a photodetector located at the other end of the fiber. An advantage of these chemically sensitive optical fibers is that the length of polymer cladding which is exposed to the sample can be as long as required, provided the fiber is able to be totally immersed in the sample. Also, the laser or LED light wavelength need not coincide with an absorption band of the chemical. Some early fiber sensors used chemical sensitive cladding polymers that were sensitive to multiple classes of chemicals, leading to a problem with cross-sensitivity to chemicals not of interest. Further response has led to fiber sensors having claddings with more specific sensitivity to the chemicals of interest.

Chip-level waveguide sensors have been developed that employ a similar chemically sensitive coating to make the selective measurement, as described for example in U.S. Pat. Nos. 5,439,647; 5,650,123 and 5,737,457 to Saini et al. The waveguide sensors are formed on chip packages containing at least one optical source and one detector. Simple sensing waveguide elements that are sensitive to an analyte of interest in a sample are removable mounted on the chip. The sensing waveguides change in a known and predictable manner in response to the presence of a specific chemical or biochemical in the sample, for example, through the use of optical absorption, fluorescence, refractive index change, any of which can be detected and measured. The chip geometries may also contain reference waveguides that are insensitive to the sample. Those chip-type sensors, while chemically specific, are limited somewhat in their sensitivity due in part to the short path length of the sample. The chemically sensitive coatings of the sensing waveguide elements must be applied very uniformly on the chip. The waveguides' active length over which is interests with the sample is limited to a few centimeters at best.

In U.S. Pat. No. 5,766,956, Groger et al. describe a diode laser-based sensor that responds directly to the presence of an analyte of interest, eliminating the need for optical coupling of laser light into an optical fiber or waveguide. The laser diode includes a sensitive coating prepared on the diode's cap layer in a surface-sensitive region positioned between a segmented top electrode. Using evanescent wave interaction with the surface-sensitive region, a change in the film thickness, refractive index or absorption alters the lasing action of the diode laser. The laser's output characteristics can be monitored using optical power measurements or spectral measurements. Changes in electrical characteristics of the laser, such as output power versus injection current, could also be monitored.

An object of the present invention is to improve the sensitivity by at least a factor of 100 of optical fiber or waveguide-based chemical sensors that use chemically sensitive optical cladding materials.

DISCLOSURE OF THE INVENTION

The object is met by magnifying the effective active length of the fiber or waveguide over which the chemically sensitive optical cladding material interacts with the light propagating within the fiber or waveguide to an equivalent length of many meters, even hundreds or thousands of meters. This is accomplished without physically increasing the actual length or size of the sensor by incorporating Bragg grating reflectors at each end of the fiber or waveguide, thereby constructing or forming an optical cavity within the fiber or waveguide, within which the injected light is trapped. Because the Bragg gratings repeatedly reflect nearly all of the light arriving at each end of the fiber or waveguide back toward the opposite end, causing the light to pass many times through the chemically sensitive fiber or waveguide before it eventually exits the fiber or waveguide, even very small changes in the optical transmission characteristics of the fiber or waveguide are magnified many fold, improving the sensing of trace amounts of a chemical of interest.

The cavity enhanced sensor includes a laser injecting light into a chemically sensitive fiber or waveguide, the fiber or waveguide itself, and a detector measuring the transmitted power output from the fiber or waveguide. The laser may be a diode laser producing several milliwatts of optical power injected into the fiber entrance. The build up of intracavity laser power within the fiber on the multitude of available frequency modes results in a net transmission of relatively high power despite the relatively low power output of the diode laser. The optical fiber or waveguide has a chemically specific polymer cladding that is sensitive to the presence of a specific chemical or class of chemicals. A Bragg grating optical cavity is formed in the fiber or waveguide to cause the light injected from the laser to pass many times through the chemically sensitive section of the fiber or waveguide. Even relatively short fibers or waveguides have equivalent sensitivity of hundreds of meters of single-pass fiber or waveguide material. The detector may be a photodiode that is sensitive to less than a nanowatt of optical power. As the detector needs only a few microwatts of power to record the cavity-enhanced fiber or waveguide signal, a typical detector dynamic range greater than 1000 is provided. The high transmission powers through the fiber or waveguide makes possible the use of inexpensive diode lasers and detectors commonly found in fiber optical communications technology.

The cavity enhancement technique is useful with any of the existing fiber optic or optical waveguide sensor schemes for sensing chemicals in air, water or other gaseous or liquid medium. It is also useful in medial diagnostic, immunoassay and similar biochemical analysis applications. The sensors can be used to analyze relatively small sample quantities.

BRIEF DESCRIPTION OF THE DRAWINGS

FIG. 1 is a schematic view of a fiber chemical sensor of the prior art.

FIG. 2 is a schematic plan view of a cavity-enhanced fiber or waveguide chemical sensor in record with the present invention.

FIG. 3 is a schematic detailed view illustrating optical interactions in a cavity-enhanced optical fiber for use in the sensor of FIG. 2.

BEST MODE OF CARRYING OUT THE INVENTION

With reference to FIG. 2, the optical sensor of the present invention includes a laser light source 21, a cavity-enhanced fiberoptic or optical waveguide 41, and a photodetector 59. The laser light source 21 is preferably a wavelength-tunable diode laser producing a beam 27 that has a narrow frequency bandwidth. A central wavelength near 1.55 $\mu$m is chosen because fiberoptic losses at this wavelength are at a minimum, and because of the wide availability of inexpensive InGaAsP laser sources (which are mass produced for the communications industry). The diode laser wavelength is rapidly modulated in optical frequency across several dozen modes of the fiber or waveguide's Bragg cavity, e.g. by modulating the current through the laser diode. In particular, the diode laser may be current regulated by a current power supply 23 that is, in turn, controlled by a fast current modulation supply 25. The two supplies 23 and 25 operate upon the diode laser 21 such that the laser output wavelength is varied about a central wavelength at a modulation frequency of from 100 Hz to 100 kHz. The wavelength variation over a modulation cycle must extend over at least two, and preferably many (e.g. several dozen), Bragg cavity Fabry-Perot longitudinal modes in the fiber or waveguide cavity. A typical fiber cavity with a 1 cm distance between the Bragg gratings 47 and 49 can be used with laser wavelength modulations of at least 0.1 nm (e.g. about 1 nm). This range of modulation is easily achieved with commercially available near infrared diode lasers. Light 27 from the diode laser 21 is turned using a beamsplitter 29 and then, by passage 31 through a lens 33, is focused into the Bragg grating fiber or waveguide 41. A reference detector 37 monitors the diode laser power 35 passing through the beamsplitter 29, thereby allowing the fiber or waveguide sensor signal 61 to be normalized by reference signal 62 to variations in laser output 27.

The optical fiber or waveguide 41 comprises a light transmission fiber or waveguide core 43 surrounded by cladding material 45 of lower refractive index than the core 43. In the preferred embodiment, the cladding 45 is comprised of a chemically-specific, chemical absorbing polymer. Such polymers include polyoxyethylene (4) lauryl ether (POELE), poly (ethyleneglycol) methyl ether (POEME), and (45–55%) glycidoxypropylmethyl dimethyl siloxane copolymer. Different polymers are responsive to specific classes of chemicals in the surrounding environment, such as hydrocarbons found in gasoline. Small changes in the index of refraction of the polymer cladding 45 result from the absorption of trace levels of specific chemicals from the environment surrounding the fiber sensor 41, and the amount of the change in the cladding refractive index is related to the amount of chemicals absorbed by the cladding polymer. The expected refractive index change can be estimated using the Clausius-Mosotti equation relating the index to the molecular weight of the polymeric cladding, however accurate measurement requires calibration using reference samples. The change can be either reversible or irreversible depending on the choice of polymer. (The polymer examples given above are reversible.) A change in the index of refraction in the cladding 45 changes the optical transmission of the fiber or waveguide 41. The fiber or waveguide 41 can be designed to detect many different types of chemicals in air or other gaseous environments, and in water, bloodstreams or other liquid environments. The specific cladding material gives rise to the specificity of the sensor, as well as contributes to the specific level of sensitivity to the chemicals of interest. Alternatively, any cladding material that changes one or more of its optical properties leading to a change in fiber or waveguide transmission as a result of exposure to specific chemicals can be used. Thus, cladding materials that respond with an increase (or decrease) in evanescent wave absorption at the laser wavelength could be used.

A pair of Bragg gratings 47 and 49 are formed in the fiber or waveguide core 43. The gratings may be fabricated using methods such as those described in U.S. Pat. Nos. 5,066,133 and 5,327,515, or by another method that produces regular variations in the index of refraction of the fiber or waveguide core 43. The Bragg gratings 47 and 49 are made to have a reflectivity greater than 99% (preferably about 99.9%) at the central output wavelength of the diode laser 21. (The reflectivity increases with the number of grating periods employed.) As illustrated in FIG. 3, light 51 from the diode laser is continuously injected into the optical fiber or waveguide Bragg cavity. Most of the light 51 is reflected by grating 47, but a small amount 55 (about 0.1%) of the light 51 passes through the first grating 47 into the cavity, where it is trapped 61 for a time determined by the mean reflectivity of the two gratings 47 and 49. (A light pulse injected into the cavity would experience several hundred to a thousand reflections, 57 and 59, by the Bragg gratings before it would be reduced to 1/e of its initial power.) The region between the two Bragg gratings 47 and 49 acts as the sensor area. The fiber or waveguide's chemically sensitive polymer cladding material 45 is present at least in this sensor area.

FIG. 1 shows that the optical fiber 13 of a chemical sensor may be placed into a sample medium in such a way that only a portion of the fiber is exposed to the sample to be sensed. This is acceptable, provided that the sensor area between the pair of Bragg gratings is the exposed portion. Areas of the fiber outside of the sensor region contribute very little to the overall signal even when also exposed to the medium. For accurate measurement, the entire length of the chemically sensitive area between the Bragg gratings should be exposed. However, if only sensing is required, without precise measurement, then just a portion of the total sensor area could be exposed, albeit with some loss of sensitivity.

As the diode laser wavelength is rapidly modulated, many mode frequency resonances of the cavity will be successively excited. When the laser wavelength matches one of the Fabry-Perot frequencies, the optical power trapped between the gratings increases rapidly, but when the laser wavelength is not matched to one of the mode frequencies, the transfer of power into the cavity between the two gratings is greatly diminished and the intracavity power is reduced to near zero. The modulation of laser wavelength increases the number of such wavelength matches from a low number of merely accidental matchings to a large number of systematic matchings in a modulation cycle, resulting in a stable average transmission through the waveguide cavity. To ensure a steady average transmission value, the laser wavelength modulation must extend over several Fabry-Perot frequency steps, or free spectral ranges, defined in frequency as $c/(2*n*L)$, where c is the speed of light, n is the index of refractive of the waveguide material, and L is the distance between the two gratings. The average transmitted power is a function of (1) the power of the diode laser source, (2) the reflectivity of the Bragg gratings in the fiber or waveguide, (3) the fraction of each diode laser modulation cycle that is resonant with one of the cavity modes, and (4) the losses per unit length of the fiber or waveguide. The preferred implementation has a constant injection diode laser power (which can in any case be normalized to account for any variations in laser output), fixed Bragg gratings, and steady average fraction of mode frequency resonances, so that the only factor changing due to the presence of a specific class of chemicals is the fiber or waveguide loss per unit length. As noted previously, that loss is determined by the relative refractive indices of the fiber or waveguide core 43 and cladding 45 materials, and by any evanescent wave 63 absorption occurring in the cladding 45 (or surrounding environment). Because of the use of a Bragg grating cavity, the fiber or waveguide loss occurs over a very long effective path length due to the multiple traversals of the light 61 reflected by the Bragg gratings 47 and 49.

Light 65 that is transmitted through the fiber or waveguide Bragg grating 49 is collected using a lens 51 and then directed by one or more mirrors or prisms 55 to a detector 59. The signal 61 from the detector 59 is monitored by a microprocessor 63, which records and stores the data for analysis. Alternatively, the data could be sent over a communications link (e.g., a wireless link) to a remote processor for the analysis. In either case, analysis determines the concentration of a chemical of interest in the environment surrounding the fiber sensor based upon the change in the fiber's optical propagation characteristics due to a defractive index change in the fiber cladding. The measurement can be calibrated using one or more reference samples of known concentration. The calibration measurement results could be stored in the form of one or more look-up tables or as co-efficients for a numerical calculation or in some other form, depending on the desired data processing technique to be used.

Accordingly, the cavity-enhanced sensor invention greatly increases the sensitivity with which chemical detection can be made. This is particularly useful for chemicals or ground water or in samples that are different to access or of limited size. The fiber sensor geometry makes it possible to insert a sensor into a sample and periodically return to make a measurement without disturbing the sample. The cavity for the fiber or waveguide sensor enhances sensitivity to hundreds of times greater than existing pass fiber or waveguide sensors. Chemical specificity of the cladding material offers a means of unambiguously detecting the presence of specific chemical classes without cross-sensitivity to other chemicals that are not of interest.

What is claimed is:

1. A chemical sensor, comprising:

a diode laser source producing laser light;

means for wavelength modulating the laser light output from the diode laser, the wavelength modulation amplitude being at least 0.1 nm and the modulation rate being at least 100 Hz;

an optical fiber waveguide having an input optically coupled to receive the modulated laser light and having an output, the optical fiber waveguide including a chemically sensitive cladding layer responsive to the presence of a specific class of chemicals in the environment around the cladding layer so as to produce a change in the cladding refractive index that alters the light propagation characteristics of the fiber waveguide, the optical fiber waveguide further including a fiber core with a pair of grating reflectors formed therein, the grating reflectors defining an optical cavity therebetween; and a photodetector optically coupled to said output of said optical fiber waveguide to receive laser light transmitted through said fiber.

2. The sensor of claim 1 wherein said cladding layer is composed of a chemically sensitive polymer material.

3. The sensor of claim 2 wherein said polymer material is selected from the group consisting of polyoxyethylene (4) lauryl ether (POELE), poly(ethyleneglycol)methyl ether (POEME), and (45–55%) glycidoxypropylmethyl dimethyl siloxane copolymer.

4. The sensor of claim 1 wherein the response of said cladding layer to the presence of chemicals is reversible.

5. The sensor of claim 1 wherein said grating reflectors have reflectivities of at least 99%.

6. The sensor of claim 1 wherein said grating reflectors are spaced apart by at least 1 cm.

7. The sensor of claim 1 wherein said modulating means comprises a modulated drive current power supply.

8. The sensor of claim 1 wherein said wavelength-modulated diode laser source has a central output wavelength at or near a minimum absorption loss wavelength of said optical fiber waveguide.

9. A sensor, comprising:
- a laser light source producing laser light and which is wavelength modulated over a plurality of optical cavity modes at a modulation rate of at least 100 Hz;
- a waveguide having an input and optically coupled to receive said laser light and having an output and, the waveguide having an environmentally sensitive cladding layer responsive to the presence of a measurand of interest in the environment around said cladding layer in a manner that alters the light propagation properties of said waveguide, the waveguide having a pair of grating reflectors formed therein and defining an optical cavity therebetween; and
- a photodetector optically coupled to said output of said waveguide to receive laser light transmitted through said waveguide.

\* \* \* \* \*